(12) United States Patent
Nam et al.

(10) Patent No.: US 11,253,598 B2
(45) Date of Patent: Feb. 22, 2022

(54) PHARMACEUTICAL COMPOSITION CONTAINING ANIONIC DRUG, AND PREPARATION METHOD THEREFOR

(71) Applicant: SAMYANG HOLDINGS CORPORATION, Seoul (KR)

(72) Inventors: Hye Yeong Nam, Cheongju-si (KR); Bong-Oh Kim, Daejeon (KR); Min-Hyo Seo, Daejeon (KR); Ji-Yeon Son, Daejeon (KR); Ji-Hye Choi, Seoul (KR); Sang Hoon Kim, Suwon-si (KR)

(*) Notice: Subject to any disclaimer, the term of this patent is extended or adjusted under 35 U.S.C. 154(b) by 0 days.

(21) Appl. No.: 15/759,943

(22) PCT Filed: Sep. 12, 2016

(86) PCT No.: PCT/KR2016/010269
§ 371 (c)(1),
(2) Date: Mar. 14, 2018

(87) PCT Pub. No.: WO2017/048018
PCT Pub. Date: Mar. 23, 2017

(65) Prior Publication Data
US 2018/0250409 A1  Sep. 6, 2018

(30) Foreign Application Priority Data

Sep. 15, 2015  (KR) .................. 10-2015-0130587
Sep. 12, 2016  (KR) .................. 10-2016-0117053

(51) Int. Cl.
| | | |
|---|---|---|
| A61K 47/34 | (2017.01) | |
| A61K 31/7088 | (2006.01) | |
| A61K 9/00 | (2006.01) | |
| C12N 15/113 | (2010.01) | |
| A61K 47/54 | (2017.01) | |
| A61K 9/107 | (2006.01) | |

(52) U.S. Cl.
CPC .......... *A61K 47/34* (2013.01); *A61K 9/0019* (2013.01); *A61K 9/1075* (2013.01); *A61K 31/7088* (2013.01); *A61K 47/543* (2017.08); *C12N 15/113* (2013.01)

(58) Field of Classification Search
CPC combination set(s) only.
See application file for complete search history.

(56) References Cited

U.S. PATENT DOCUMENTS

| | | |
|---|---|---|
| 6,458,382 B1 | 10/2002 | Herweijer et al. |
| 2002/0086356 A1 | 7/2002 | Tuschl et al. |
| 2004/0115254 A1 | 6/2004 | Niedzinski et al. |
| 2008/0260850 A1* | 10/2008 | Yi .................... A61P 43/00 424/501 |
| 2009/0312402 A1* | 12/2009 | Contag .............. A61K 9/5123 514/44 R |
| 2011/0257253 A1 | 10/2011 | Seo et al. |
| 2013/0266641 A1 | 10/2013 | Choi et al. |
| 2014/0294932 A1 | 10/2014 | Kim et al. |

FOREIGN PATENT DOCUMENTS

| | | |
|---|---|---|
| EP | 2377517 A2 | 10/2011 |
| EP | 2591792 A1 | 5/2013 |
| JP | 2007-536219 A | 12/2007 |
| JP | 2012-513460 A | 6/2012 |
| KR | 10-2010-0076863 A | 7/2010 |
| KR | 10-2011-0077818 A | 7/2011 |
| KR | 10-2012-0078661 A | 7/2012 |
| KR | 10-1296326 B1 | 8/2013 |
| WO | WO 97/10849 A1 | 3/1997 |
| WO | WO 03/059382 A2 | 7/2003 |
| WO | WO 2005/107813 A1 | 11/2005 |
| WO | WO 2009/078685 A2 | 6/2009 |
| WO | WO 2010/074380 A1 | 7/2010 |
| WO | WO 2012/005376 A1 | 1/2012 |
| WO | WO 2012/091523 A2 | 7/2012 |
| WO | WO-2013151326 A1 * | 10/2013 ............. C12N 15/88 |
| WO | WO 2014/169007 A2 | 10/2014 |

OTHER PUBLICATIONS

Machine Translation of KR 10-2011-0077818 (Year: 2011).*
De Paula et al., "Hydrophobization and Bioconjugation for Enhanced siRNA Delivery and Targeting," RNA, vol. 13, No. 4, 2007, pp. 431-456.
Elbashir et al., "RNA Interference is Mediated by 21- and 22-nucleotide RNAs," Genes & Development, vol. 15, 2001, pp. 188-200.
Gary et al., "Polymer-based siRNA Delivery: Perspectives on the Fundamental and Phenomenological Distinctions from Polymer-based DNA Delivery," Journal of Controlled Release, vol. 121, 2007 (Available online May 26, 2007), pp. 64-73.
McManus et al., "Gene Silencing in Mammals by Small Interfering RNAs," Nature Reviews, Genetics, vol. 3, Oct. 2002, pp. 737-747.
Extended European Search Report dated Apr. 4, 2019 for Application No. 16846839.5.
International Search Report (PCT/ISA/210) issued in PCT/KR2016/010269, dated Dec. 21, 2016.

* cited by examiner

*Primary Examiner* — Richard A Schnizer
(74) *Attorney, Agent, or Firm* — Birch, Stewart, Kolasch & Birch, LLP

(57) ABSTRACT

Disclosed are a pharmaceutical composition for anionic drug delivery, and a preparation method therefor, the pharmaceutical composition for anionic drug delivery containing: an anionic drug as an active ingredient; a cationic compound; an amphiphilic block copolymer; and a polylactate, wherein the anionic drug formed a complex with the cationic lipid, and the complex is encapsulated within a micelle structure formed by the amphiphilic block copolymer and the polylactate.

15 Claims, 2 Drawing Sheets

{FIGURE 1}
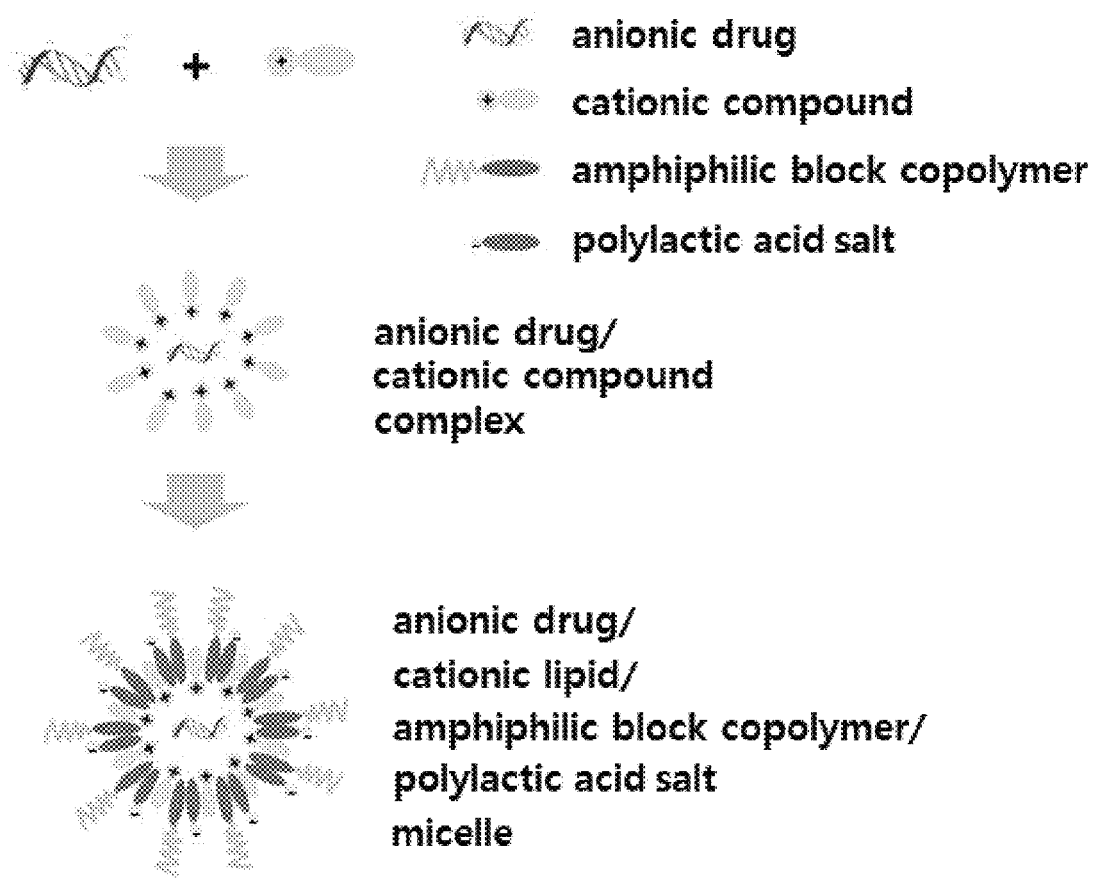

[FIGURE 2]
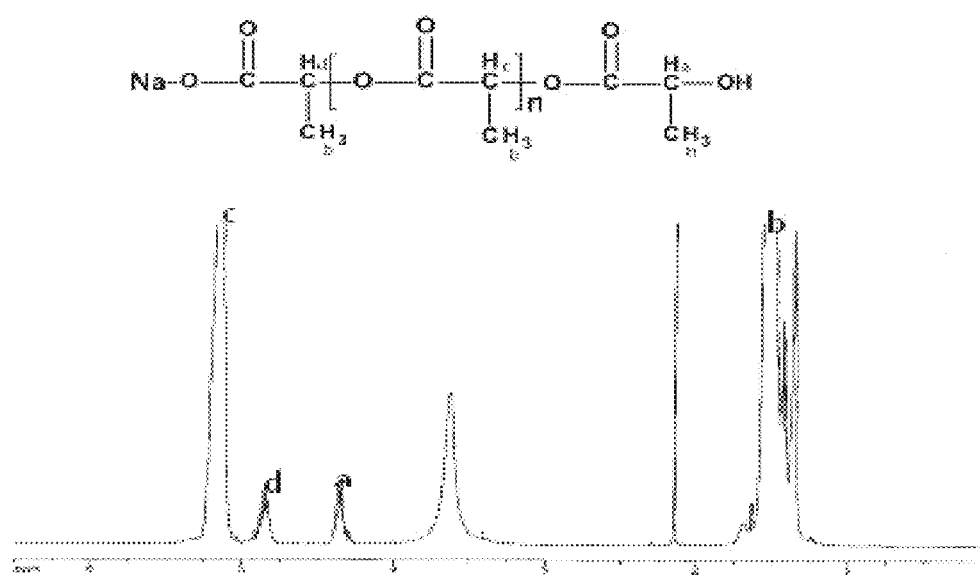

PHARMACEUTICAL COMPOSITION CONTAINING ANIONIC DRUG, AND PREPARATION METHOD THEREFOR

TECHNICAL FIELD

This disclosure relates to a pharmaceutical composition containing anionic drug and delivering it, and a method for preparing the same.

BACKGROUND ART

Safe and efficient drug delivery technologies have been studied for a long time for treatment using anionic drugs, particularly nucleic acid, and various delivery systems and delivery technologies have been developed. Particularly, delivery technologies using a viral delivery system using adenovirus or retrovirus, etc., and a non-viral delivery system using cationic lipids, cationic polymers, etc. have been developed.

However, a technology using a viral delivery system is exposed to risks such as non-specific immune reaction, etc., and it is known to have many problems in commercialization due to the complex production process. Therefore, recent studies have progressed toward a non-viral delivery system using cationic lipids or cationic polymers to overcome these disadvantages. Although the non-viral delivery system is less efficient than the viral delivery system, it has fewer side effects and the production is less expensive than the viral delivery system.

Many studies have been conducted on non-viral delivery system used for delivery of nucleic acid, and most representative examples thereof include a complex of cationic lipid and nucleic acid (lipoplex) and a complex of a polycationic polymer and nucleic acid (polyplex). Many studies on cationic lipids or polycationic polymers have been made because they stabilize anionic drugs by forming a complex by electrostatic interactions with the anionic drug, and facilitates delivery into cells (De Paula D, Bentley M V, Mahato R I, Hydrophobization and bioconjugation for enhanced siRNA delivery and targeting, RNA 13 (2007) 431-56; Gary D J, Puri N, Won Y Y, Polymer-based siRNA delivery: Perspectives on the fundamental and phenomenological distinctions from polymer-based DNA delivery, J Control Release 121 (2007) 64-73).

However, if the cationic lipids or polycationic polymers studied so far are used in an amount required to obtain sufficient effects, serious toxicity, although less than with the viral delivery system, may result and thus it may be improper for therapeutic use. And although a lipid-nucleic acid complex that forms a complex through a bond between a cationic lipid and a nucleic acid to deliver the nucleic acid into cells is widely used in cell line experiments, it does not form a structure that can be stable in blood, and thus it cannot be used in the living body (see U.S. Pat. No. 6,458,382).

Furthermore, the delivery system using the nucleic acid directly conjugated with a lipid or a polymer is being studied, but if a lipid or a polymer is directly conjugated with nucleic acid, there are difficulties in terms of conjugation efficiency or quality control. In addition, the efficiency of nucleic acid delivery has not yet been clearly validated.

Therefore, it is required to develop an anionic drug delivery technology using the minimal amount of cationic polymer or cationic lipid to decrease toxicity, which is stable in blood and body fluid, and enabling delivery into cells to obtain sufficient effects. Meanwhile, there have been various attempts to use amphiphilic block copolymer as a drug delivery system that can solubilize a poorly water-soluble drug by forming a polymeric micelle and stabilize a poorly water-soluble drug in an aqueous solution (International Publication No. WO 1997/010849). This amphiphilic block copolymer may solubilize a hydrophobic poorly water-soluble drug by forming a polymeric micelle having hydrophobic inner part. However, because a hydrophilic drug such as an anionic nucleic acid cannot be entrapped in the polymeric micelle, it is not suitable for delivery of an anionic drug including a nucleic acid. There was also a disclosure of a composition for delivery of anionic drug which forms a complex of a nucleic acid and a cationic lipid by electrostatic interaction to entrap the complex in the micelle structure of the amphiphilic block copolymer. However, improvements are needed in terms of stability of nucleic acid in blood and specific targeting of cancer tissues.

Korean Patent No. 1296326 discloses a composition for delivery of an anionic drug comprising an anionic drug; a cationic lipid; an amphiphilic block copolymer and a polylactic acid, wherein the anionic drug forms a complex with the cationic lipid, and the complex is entrapped in the micelle structure of the amphiphilic block copolymer and polylactic acid. However, because the polylactic acid used in this patent is a conventional polylactic acid polymer having carboxyl group at the end, drug delivery is not efficient.

Meanwhile, many diseases result from the overexpression of disease genes or the expression of mutated genes. Since siRNA (short interfering RNA) inhibits the expression of specific genes in a sequence-specific manner, it is highlighted as a therapeutic nucleic acid drug. Particularly, siRNA is expected to overcome the problems of the antisense nucleotide or ribozyme because siRNA has more potency and more accurate gene selectivity than the antisense nucleotide or ribozyme. The siRNA is a short double-stranded RNA molecule, and it inhibits the expression of corresponding genes by cleaving the mRNA of genes having a sequence complementary thereto (McManus and Sharp, Nature Rev. Genet. 3:737 (2002); Elbashir, et al., Genes Dev. 15:188 (2001)).

However, despite these advantages, siRNA is known to be rapidly degraded by nuclease in blood and rapidly excreted from the body through the kidneys. It is also known that siRNA cannot easily pass a cell membrane because it is strongly negatively charged. Therefore, to use siRNA as a therapeutic agent, it is required to develop a delivery system that may stabilize siRNA in blood, efficiently deliver it into target cells or tissues, and yet not show toxicity.

CONTENTS OF THE INVENTION

Problems to be Solved

To resolve the problems described above, one object of the present invention is to provide a composition for delivering an anionic drug, comprising a micelle structure containing a salt of polylactic acid so as to effectively deliver anionic drugs into the body.

Another object of the present invention is to provide the use of the composition for delivering anionic drugs.

A further object of the present invention is to provide a method for delivering anionic drugs comprising administering the composition.

A still further object of the present invention is to provide a method for preparing a pharmaceutical composition capable of effectively delivering anionic drugs into the body.

Technical Means to Solve the Problems

One embodiment of the present invention relates to a composition for delivering an anionic drug comprising a micelle structure containing a salt of polylactic acid so as to effectively deliver anionic drugs into the body, a use of the composition for delivering anionic drugs, and a method for delivering anionic drugs comprising administering the composition.

The composition for delivering an anionic drug containing the micelle structure according to an embodiment of the present invention comprises a micelle structure of an amphiphilic block copolymer and a salt of polylactic acid, which includes a complex of a drug and a cationic compound. Specifically, the composition comprises an anionic drug as an active ingredient; a cationic compound; an amphiphilic block copolymer; and a salt of polylactic acid, wherein the anionic drug forms a complex with the cationic compound by electrostatic interaction, and the complex is entrapped in the micelle structure of the amphiphilic block copolymer and the salt of polylactic acid.

The composition is water-soluble and contains a salt of polylactic acid as a component of the micelle structure. Therefore, in case of administration into the body, the composition has increased blood stability and it can be efficiently delivered to a target site, especially cancer tissue, by avoiding the reticuloendothelial system (RES). Hence, the composition would be useful for avoiding RES and/or improvement of targeting.

As another embodiment of the present invention, a method for preparing the composition for delivering an anionic drug may comprise (a) dissolving an anionic drug, a cationic compound, an amphiphilic block copolymer and a salt of polylactic acid in a water-miscible organic solvent or a mixed solvent of an aqueous solution and an organic solvent; (b) removing a layer of organic solvent from step (a); and (c) adding an aqueous solution to the mixture from step (b) in which the organic solvent is removed, to form micelles.

Effects of the Invention

The pharmaceutical composition for delivering an anionic drug according to an embodiment of the present invention is able to improve stability of the anionic drug in blood or body fluid by isolating the anionic drug from external environment by using a cationic compound and a micelle structure composed of an amphiphilic block copolymer and a salt of polylactic acid. Therefore, the pharmaceutical composition is able to improve stability of the anionic drug in blood or body fluid when administered into the body. Especially, the pharmaceutical composition helps the anionic drug to avoid the reticuloendothelial system (RES) so as to be efficiently delivered into cells.

BRIEF EXPLANATION OF THE DRAWINGS

FIG. 1 is a schematic structure of the polymer micelle delivery system in which the anionic drug and the cationic compound are entrapped according to an embodiment of the present invention.

FIG. 2 is an NMR measurement result of PLANa prepared according to Preparation Example 8.

MODES FOR THE INVENTION

Hereinafter, the present invention will be explained in detail.

Among the components of the composition of an embodiment of the present invention, the anionic drug and the cationic compound are entrapped in the micelle structure of the amphiphilic block copolymer and the salt of polylactic acid. A schematic structure of the polymer micelle system, in which the anionic drug and the cationic compound are entrapped, is shown in FIG. 1. Referring to FIG. 1, a complex of the anionic drug and the cationic compound is formed by electrostatic interaction between the anionic drug and the cationic compound. The formed complex of the anionic drug and the cationic compound are entrapped in the micelle structure of the amphiphilic block copolymer and the salt of polylactic acid.

As shown in FIG. 1, the micelle structure is formed from the amphiphilic block copolymer and the salt of polylactic acid. Under aqueous environment, the hydrophilic part of the amphiphilic block copolymer forms the outer wall of the micelle, and the hydrophobic part of the amphiphilic block copolymer and a salt of polylactic acid, an independent ingredient, form the inner wall of the micelle. The anionic drug and the cationic compound are entrapped inside the formed micelle. The complex of the anionic drug and the cationic compound is entrapped in the micelle structure formed from the amphiphilic block copolymer and the salt of polylactic acid, so it may have improved stability in blood or body fluid. According to one embodiment, the particle size of the micelle may be 10 to 200 nm, preferably 10 to 150 nm. In addition, the standard charge of the micelle particle may be −20 to 20 mV, preferably −10 to 10 mV. The particle size and the standard charge are determined considering the stability of the micelle structure, contents of the constitutional ingredients, absorption of anionic drugs in a body, and convenience of sterilization as a pharmaceutical composition.

The anionic drug as an active ingredient in the composition of an embodiment of the present invention may include any material that is negatively charged in an aqueous solution and has pharmacological activity. According to one embodiment, the anionic property may be provided from at least one functional group selected from the groups consisting of carboxylic group, phosphate group and sulfate group. According to one embodiment, the anionic drug may be a multi-anionic drug such as a peptide, a protein or a heparin, or a nucleic acid.

In addition, the nucleic acid may be a deoxyribonucleic acid, a ribonucleic acid, or a nucleic acid drug in which the backbone, sugar or base is chemically modified or the end is modified. More specific examples may be a nucleic acid selected from the group consisting of RNA, DNA, siRNA, aptamer, antisense ODN (oligodeoxynucleotide), antisense RNA, ribozyme and DNAzyme, etc. And the backbone, sugar or base of the nucleic acid may be chemically modified or the end may be modified for the purpose of increasing blood stability or weakening immune reactions, and the like. Specifically, a part of phosphodiester bond of nucleic acid may be substituted with phosphorothioate or boranophosphate bond, or 2'-OH positions of a part of ribose bases may include at least one kind of modified nucleotide to which various functional groups such as methyl group, methoxyethyl group, fluorine, and the like are introduced.

Furthermore, at least one end of the nucleic acid may be modified with one or more selected from the group consisting of cholesterol, tocopherol and $C_{10\text{-}24}$ fatty acid. In case of siRNA, for example, 5' or 3' end, or both ends of the sense and/or antisense strand may be modified, and preferably the end of the sense strand may be modified.

The cholesterol, tocopherol and $C_{10-24}$ fatty acid may include analogues, derivatives and metabolites thereof.

The siRNA refers to duplex RNA or single-strand RNA having a double-stranded form in the single-strand RNA, which may reduce or inhibit the expression of a target gene by mediating degradation of mRNA complementary to the sequence of siRNA if siRNA exists in the same cell as the target gene does. The bond between the double strands is made by a hydrogen bond between nucleotides, not all nucleotides in the double strands should be complementarily bound with the corresponding nucleotides, and both strands may be separated or may not be separated. According to one embodiment, the length of the siRNA may be about 15 to 60 nucleotides (meaning the number of nucleotides of one double-stranded RNA, i.e., the number of base pairs, and in the case of a single-stranded RNA, it means the length of double strands in the single stranded RNA), specifically about 15 to 30 nucleotides, and more specifically about 19 to 25 nucleotides.

According to one embodiment, the double-stranded siRNA may have an overhang of 1-5 nucleotides at one or both ends of the 3' or 5' end. According to another embodiment, it may be blunt without an overhang at both ends. Specifically, it may be siRNA disclosed in U.S. Patent Publication No. 2002/0086356 or U.S. Pat. No. 7,056,704 (incorporated herein by references).

In addition, the siRNA may have a symmetrical structure with the same lengths of two strands, or it may have a non-symmetrical structure with one strand shorter than the other. Specifically, it may be a non-symmetrical siRNA molecule of double strands consisting of 19 to 21 nucleotide (nt) antisense; and 15 to 19 nt sense having a sequence complementary to the antisense, wherein the 5' end of the antisense is the blunt end, and the 3' end of the antisense has a 1-5 nucleotide overhang. Specifically, it may be siRNA disclosed in International Publication No. WO 09/078685.

The anionic drug of an embodiment of the present invention is preferably included in the content of 0.001 to 10 wt %, specifically 0.01 to 5 wt %, based on the total weight of the composition. If the content is less than 0.001 wt %, the amount of delivery system is too large compared to the drug, and thus, side effects may be caused by the delivery system. If it exceeds 10 wt %, the stability of the micelle may be decreased and loss rate during filter sterilization may be increased because the micelle is too big.

According to one embodiment, the cationic compound forms a complex with the anionic drug by electrostatic interactions, and the complex is entrapped in the micelle structure of the amphiphilic block copolymer. Therefore, the cationic compound may include any type of compound capable of forming a complex with the anionic drug by electrostatic interaction, and for example, may include lipids and polymers. The cationic lipid may include N,N-dioleyl-N,N-dimethylammoniumchloride (DODAC), N,N-distearyl-N,N-dimethylammoniumbromide (DDAB), N-(1-(2,3-dioleoyloxy)propyl-N,N,N-trimethylammoniumchloride (DOTAP), N,N-dimethyl-(2,3-dioleoyloxy)propylamine (DODMA), N,N,N-trimethyl-(2,3-dioleoyloxy)propylamine (DOTMA), 1,2-diacyl-3-trimethylammonium-propane (TAP), 1,2-diacyl-3-dimethylammonium-propane (DAP), 3β-[N-(N',N',N'-trimethylaminoethane)carbamoyl]cholesterol (TC-cholesterol), 3β-[N-(N',N'-dimethylaminoethane)carbamoyl]cholesterol (DC-cholesterol), 3β-[N-(N'-monomethylaminoethane)carbamoyl]cholesterol (MC-cholesterol), 3β-[N-(aminoethane)carbamoyl]cholesterol (AC-cholesterol), cholesteryloxypropane-1-amine (COPA), N-(N'-aminoethane)carbamoylpropanoic tocopherol (AC-tocopherol), N-(N'-methylaminoethane)carbamoylpropanoic tocopherol (MC-tocopherol), or a combination thereof. If such a cationic lipid is used, to decrease toxicity induced by cationic lipid, it may be preferable to use less polycationic lipid having high charge density, and more specifically, only one functional group capable of exhibiting positive charge in an aqueous solution may be included in a molecule. Therefore, in a preferable embodiment, the cationic lipid may be at least one selected from the group consisting of 3β-[N-(N',N',N'-trimethylaminoethane)carbamoyl]cholesterol (TC-cholesterol), 3β-[N-(N',N'-dimethylaminoethane)carbamoyl]cholesterol (DC-cholesterol), 3β-[N-(N'-monomethylaminoethane)carbamoyl]cholesterol (MC-cholesterol), 3β-[N-(aminoethane)carbamoyl]cholesterol (AC-cholesterol), N-(1-(2,3-dioleoyloxy)propyl-N,N,N-trimethylammoniumchloride (DOTAP), N,N-dimethyl-(2,3-dioleoyloxy)propylamine (DODMA) and N,N,N-trimethyl-(2,3-dioleoyloxy)propylamine (DOTMA). On the other hand, the cationic polymer may be selected from the group consisting of chitosan, glycol chitosan, protamine, polylysine, polyarginine, polyamidoamine (PAMAM), polyethylenimine, dextran, hyaluronic acid, albumin, polymer polyethylenimine (PEI), polyamine and polyvinylamine (PVAm), and preferably may be at least one selected from polymer polyethylenimine (PEI), polyamine and polyvinylamine (PVA).

In one embodiment, the cationic lipid may be represented by the following Formula 7:

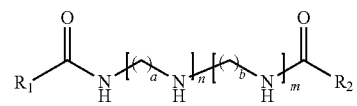

[Formula 7]

wherein n and m each are 0 to 12 with the proviso that $2 \leq n+m \leq 12$, a and b each are 1 to 6, and $R_1$ and $R_2$ each are independently selected from the group consisting of saturated and unsaturated $C_{11-25}$ hydrocarbons. Preferably, n and m may be independently 1 to 9, and $2 \leq n+m \leq 10$. Preferably, a and b are 2 to 4.

Preferably, $R_1$ and $R_2$ are independently selected from the group consisting of lauryl, myristyl, palmityl, stearyl, arachidyl, behenyl, lignoceryl, cerotyl, myristoleyl, palmitoleyl, sapienyl, oleyl, linoleyl, arachidonyl, eicosapentaenyl, erucyl, docosahexaenyl and cerotyl.

Specific examples of the cationic lipid may be at least one selected from the group consisting of 1,6-dioleoyl triethylene tetramide, 1,8-dilinoleoyl tetraethylene pentamide, 1,4-dimyristoleoyl diethylene triamide, 1,10-distearoyl pentaethylene hexamide and 1,10-dioleoyl pentaethylene hexamide.

The cationic compound used in an embodiment of the present invention may be included in the content of 0.01 to 50 wt %, and specifically 0.1 to 10 wt % based on the total weight of the composition. If the content is less than 0.01 wt %, it may not be sufficient to form a complex with the anionic drug. If it exceeds 50 wt %, the micelle may be too large and thus stability of the micelle may be decreased and loss rate during filter sterilization may be increased.

The cationic compound binds with the anionic drug by electrostatic interactions so as to form a complex. According to one embodiment, the ratio of quantities of electric charge of the cationic compound (N) and the anionic drug (P) (N/P: the ratio of the positive electric charge of the cationic compound to the negative electric charge of the anionic drug) is 0.1 to 128, specifically 0.5 to 64, more specifically 1 to 32, far more specifically 1 to 24, and most specifically 6 to 24. If the ratio (N/P) is less than 0.1, it may be difficult to form a complex including a sufficient amount of anionic drug. On the other hand, if the ratio (N/P) exceeds 128, toxicity may be induced.

According to one embodiment, the amphiphilic block copolymer may be an A-B type block copolymer including a hydrophilic A block and a hydrophobic B block. The A-B type block copolymer forms a core-shell type polymeric micelle in an aqueous solution, wherein the hydrophobic B block forms a core (an inner wall) and the hydrophilic A block forms a shell (an outer wall).

In this regard, the hydrophilic A block may be at least one selected from the group consisting of polyalkyleneglycol, polyvinyl alcohol, polyvinyl pyrrolidone, polyacrylamide, and derivatives thereof. The hydrophilic A block may be at least one selected from the group consisting of monomethoxy polyethylene glycol, monoacetoxy polyethylene glycol, polyethylene glycol, a copolymer of polyethylene and propylene glycol, and polyvinyl pyrrolidone. The hydrophilic A block may have a number average molecular weight of 200 to 50,000 Dalton, specifically 1,000 to 20,000 Dalton, and more specifically 1,000 to 5,000 Dalton.

If necessary, a functional group or a ligand that may bind to a specific tissue or cell, or a functional group capable of promoting intracellular delivery may be chemically conjugated to the end of the hydrophilic A block so as to control the distribution of the polymeric micelle delivery system which is formed from the amphiphilic block copolymer and the salt of polylactic acid in a body, or to increase the efficiency of delivery of the micelle delivery system into cells. The functional group or ligand may be at least one selected from the group consisting of monosaccharide, polysaccharide, vitamins, peptides, proteins, and an antibody to a cell surface receptor. In more specific examples, the functional group or ligand may be at least one selected from the group consisting of anisamide, vitamin B9 (folic acid), vitamin B12, vitamin A, galactose, lactose, mannose, hyaluronic acid, RGD peptide, NGR peptide, transferrin, an antibody to a transferrin receptor, etc.

The hydrophobic B block is a biocompatible and biodegradable polymer, and it may be at least one selected from the group consisting of polyester, polyanhydride, polyamino acid, polyorthoester, and polyphosphazine. More specific examples thereof may include polylactide, polyglycolide, polycaprolactone, polydioxane-2-one, a copolymer of polylactide and glycolide, a copolymer of polylactide and polydioxane-2-one, a copolymer of polylactide and polycaprolactone, and a copolymer of polyglycolide and polycaprolactone. According to another embodiment, the hydrophobic B block may have a number average molecular weight of 50 to 50,000 Dalton, specifically 200 to 20,000 Dalton, and more specifically 1,000 to 5,000 Dalton. And to increase hydrophobicity of the hydrophobic block for improving the stability of the micelle, tocopherol, cholesterol, or $C_{10-24}$ fatty acid may be chemically conjugated to a hydroxyl group at the end of the hydrophobic block.

The amphiphilic block copolymer comprising the hydrophilic block (A) and the hydrophobic block (B) may be included in the content of 40 to 99.98 wt %, specifically 85 to 99.8 wt %, and more specifically 90 to 99.8 wt %, based on the total dry weight of the particle. If the content of the amphiphilic block copolymer is less than 40 wt %, the micelle may become so large that the stability of the micelle may be decreased and the loss during filter sterilization may be increased. If it exceeds 99.98 wt %, the content of anionic drug that can be incorporated may become too small.

According to another embodiment, the amphiphilic block copolymer may include 40 to 70 wt % of the hydrophilic block (A), and specifically 50 to 60 wt % of the hydrophilic block (A), based on the weight of the copolymer. If the ratio of the hydrophilic block (A) is less than 40 wt %, solubility of the polymer in water is low, and thus it may be difficult to form a micelle. Therefore, the ratio of the hydrophilic block (A) is preferably no less than 40 wt % to give sufficient water solubility for the copolymer to form a micelle. If it exceeds 70 wt %, hydrophilicity may be too high and thus stability of the polymeric micelle may become too low, and it may be difficult to solubilize a complex of the anionic drug and the cationic lipid. Therefore, in light of the stability of the micelle, the ratio of the hydrophilic block (A) is preferably no more than 70 wt %.

According to one embodiment, the amphiphilic block copolymer allows enclosure of the complex of the anionic drug and the cationic lipid in the micelle structure in an aqueous solution, wherein the ratio of the weight of the complex of the anionic drug and the cationic lipid (a) to the weight of the amphiphilic block copolymer (b) [a/b×100; (the weight of the anionic drug+the weight of the cationic lipid)/the weight of the amphiphilic block copolymer×100] may be 0.001 to 100 wt %, specifically 0.01 to 50 wt %, and more specifically 0.1 to 10 wt %. If the weight ratio is less than 0.001 wt %, the content of the complex of the anionic drug and the cationic lipid may become too low, and thus it may be difficult to provide enough content of the anionic drug. If it exceeds 100 wt %, a micelle structure of appropriate size may not be formed considering the molecular weight of the amphiphilic block copolymer and the amount of the complex of the anionic drug and the lipid.

The micelle structure in the composition according to an embodiment of the present invention comprises a salt of polylactic acid (e.g. PLANa). The salt of polylactic acid is distributed to the core (inner wall) of the micelle so as to enhance hydrophobicity of the core and stabilize the micelle, and at the same time, help avoid reticuloendothelial system (RES) in the body. That is, an anion of carboxylic acid in the salt of polylactic acid efficiently binds to the cationic complex so as to decrease the surface charge of the polymeric micelle. Thereby, positive charge of the surface potential of a polymeric micelle would be less than that of a polymeric micelle that does not contain a salt of polylactic acid, and thus it may be less captured by reticuloendothelial system and efficiently delivered to target sites (e.g., cancer cells, inflammatory cells, etc.).

The salt of polylactic acid, which is an independent component from the amphiphilic block copolymer, is a component of an inner wall of the micelle and may have a number average molecular weight of 500 to 50,000 Dalton, and specifically 1,000 to 50,000 Dalton. If the number average molecular weight is less than 500 Dalton, the salt of polylactic acid does not easily exist at the core (inner wall) of the micelle because the hydrophobicity is too low. If the number average molecular weight exceeds 50,000 Dalton, the polymeric micelle may be too big.

The salt of polylactic acid may be used in 10 to 200 parts by weight, specifically 10 to 100 parts by weight, and more specifically 30 to 60 parts by weight per 100 parts by weight of the amphiphilic block copolymer. If the content of the salt of polylactic acid exceed 200 parts by weight per 100 parts by weight of the amphiphilic block copolymer, the size of the micelle may be too large and thus sterilized membrane filtration becomes difficult. If the content of the salt of polylactic acid is less than 1 part by weight per 100 parts by weight of the amphiphilic block copolymer, it is hard to obtain the desired effect.

According to one embodiment, the composition of an embodiment of the present invention may comprise 10 to 1,000 parts by weight of the amphiphilic block copolymer and 5 to 500 parts by weight of the a salt of polylactic acid per 1 part by weight of the anionic drug. Preferably, the amphiphilic block copolymer may be 50 to 800 parts by weight, and more preferably 100 to 500 parts by weight. Preferably, the salt of polylactic acid may be 10 to 300 parts by weight, and more preferably 50 to 100 parts by weight.

According to one embodiment, the end of the salt of polylactic acid opposite to the end where the salt is formed may be substituted with one selected from the group consisting of hydroxyl, acetoxy, benzoyloxy, decanoyloxy, palmitoyloxy, and $C_{1-2}$ alkoxy.

According to one preferred embodiment, the salt of polylactic acid may be selected from the group consisting of Formulae 1 to 6 as below.

  [Formula 1]

wherein A is —COO—CHZ—; B is —COO—CHY—, —COO—CH$_2$CH$_2$CH$_2$CH$_2$— or —COO—CH$_2$CH$_2$OCH$_2$—; R is a hydrogen atom, or acetyl, benzoyl, decanoyl, palmitoyl, methyl or ethyl; Z and Y each are a hydrogen atom, or methyl or phenyl; M is Na, K or Li; n is an integer from 1 to 30; and m is an integer from 0 to 20;

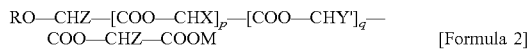  [Formula 2]

wherein X is methyl; Y' is a hydrogen atom or phenyl; p is an integer from 0 to 25, q is an integer from 0 to 25, with the proviso that p+q is an integer from 5 to 25; R is a hydrogen atom, or acetyl, benzoyl, decanoyl, palmitoyl, methyl or ethyl; M is Na, K or Li; and Z is a hydrogen atom, methyl or phenyl;

  [Formula 3]

wherein W-M' is

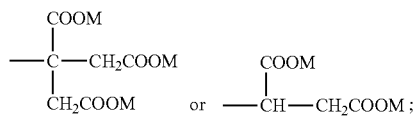

PAD is selected from the group consisting of D,L-polylactide, D-polylactide, polymandelic acid, copolymer of D,L-lactide and glycolic acid, copolymer of D,L-lactide and mandelic acid, copolymer of D,L-lactide and caprolactone, and copolymer of D,L-lactide and 1,4-dioxane-2-one; R is a hydrogen atom, or acetyl, benzoyl, decanoyl, palmitoyl, methyl or ethyl; and M is independently Na, K or Li;

  [Formula 4]

wherein S is

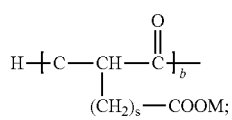

L is —NR$_1$— or -O-, wherein R$_1$ is a hydrogen atom or $C_{1-10}$ alkyl; Q is CH$_3$, CH$_2$CH$_3$, CH$_2$CH$_2$CH$_3$, CH$_2$CH$_2$CH$_2$CH$_3$, or CH$_2$C$_6$H$_5$; a is an integer from 0 to 4; b is an integer from 1 to 10; M is Na, K or Li; and PAD is at least one selected from the group consisting of D,L-polylactide, D-polylactide, polymandelic acid, copolymer of D,L-lactide and glycolic acid, copolymer of D,L-lactide and mandelic acid, copolymer of D,L-lactide and caprolactone, and copolymer of D,L-lactide and 1,4-dioxane-2-one;

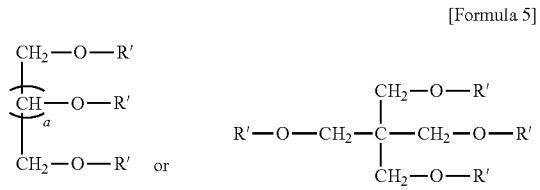  [Formula 5]

wherein R' is -PAD-O—C(O)—CH$_2$CH$_2$—C(O)—OM, wherein PAD is selected from the group consisting of D,L-polylactide, D-polylactide, polymandelic acid, copolymer of D,L-lactide and glycolic acid, copolymer of D,L-lactide and mandelic acid, copolymer of D,L-lactide and caprolactone, and copolymer of D,L-lactide and 1,4-dioxane-2-one, M is Na, K or Li; and a is an integer from 1 to 4; and

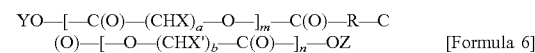  [Formula 6]

wherein X and X' are independently hydrogen, $C_{1-10}$ alkyl or $C_{6-20}$ aryl; Y and Z are independently Na, K or Li; m and n are independently an integer from 0 to 95, with the proviso that 5<m+n<100; a and b are independently an integer from 1 to 6; and R is —(CH$_2$)$_k$—, $C_{2-10}$ divalent alkenyl, $C_{6-20}$ divalent aryl or a combination thereof, wherein k is an integer from 0 to 10.

The salt of polylactic acid is preferably the compound of Formula 1 or Formula 2.

In one embodiment of the present invention, the composition may further comprise a fusogenic lipid in an amount of 0.01 to 50 wt %, and specifically 0.1 to 10 wt % based on total weight of the composition, for increasing delivery efficiency of the anionic drug into cells.

The fusogenic lipid forms a complex of the anionic drug, the cationic lipid and the fusogenic lipid by an electrostatic interaction when it is mixed with the complex of the anionic drug and the cationic lipid. The complex containing the fusogenic lipid is entrapped in the micelle structure of the amphiphilic block copolymer. In one embodiment, the fusogenic lipid may be selected from the group consisting of phospholipid, cholesterol, tocopherol and combinations thereof.

Specifically, the phospholipid may be at least one selected from the group consisting of phosphatidylethanolamin (PE), phosphatidylcholine (PC) and phosphatidic acid. The phosphatidylethanolamin (PE), phosphatidylcholine (PC) and phosphatidic acid may be in a form combined with one or two $C_{10-24}$ fatty acids. The cholesterol and tocopherol may include analogues, derivatives and metabolites of each of the cholesterol and tocopherol.

Specifically, the fusogenic lipid may be selected from the group consisting of dilauroyl phosphatidylethanolamine, dimyristoyl phosphatidylethanolamine, dipalmitoyl phosphatidylethanolamine, distearoyl phosphatidylethanolamine, dioleoyl phosphatidylethanolamine, dilinoleoyl phosphatidylethanolamine, 1-palmitoyl-2-oleoyl phosphatidylethanolamine, 1,2-diphytanoyl-3-sn-phosphatidylethanolamine, dilauroyl phosphatidylcholine, dimyristoyl phosphatidylcholine, dipalmitoyl phosphatidylcholine, distearoyl phosphatidylcholine, dioleoyl phosphatidylcholine, dilinoleoyl phosphatidylcholine, 1-palmitoyl-2-oleoyl phosphatidylcholine, 1,2-diphytanoyl-3-sn-phosphatidylcholine, dilauroyl phosphatidic acid, dimyristoyl phosphatidic acid, dipalmitoyl phosphatidic acid, distearoyl phosphatidic acid, dioleoyl phosphatidic acid, dilinoleoyl phosphatidic acid, 1-palmitoyl-2-oleoyl phosphatidic acid, 1,2-diphytanoyl-3-sn-phosphatidic acid, cholesterol, tocopherol and combinations thereof.

According to one preferred embodiment, the fusogenic lipid may be at least one selected from the group consisting of dioleoyl phosphatidylethanolamine (DOPE), 1,2-dipalmitoleoyl-sn-glycero -3-phosphocholine (DPPC), 1,2-dioleoyl-sn-glycero-3-phosphocholine (DOPC) and 1,2-dipalmitoleoyl-sn-glycero-3-phosphoethanolamine (DPPE), etc.

According to one embodiment of the present invention, the composition, which contains the anionic drug-cationic compound complex entrapped in the micelle structure of the amphiphilic block copolymer and the salt of polylactic acid, may be administered in the route of blood vessel, muscle, subcutaneous, oral, bone, transdermal or local tissue, and the like, and it may be formulated into various oral or parenteral administration formulations. Examples of the oral administration formulation may include tablets, capsules, powder and liquid, and the examples of the parenteral administration formulation may include eye drop and injection. According to one preferred embodiment, the composition may be a formulation for injection. For example, if the compound is lyophilized, it may be reconstituted with distilled water for injection, 0.9% physiological saline, 5% dextrose aqueous solution, and the like, to formulate into an injection formulation.

Another embodiment of the present invention provides a method for preparing the pharmaceutical composition comprising the amphiphilic block copolymer micelle containing the anionic drug.

According to one embodiment, the method for preparing the composition for delivering an anionic drug containing the anionic drug, the cationic lipid, the amphiphilic block copolymer and the salt of polylactic acid may comprise:

(a) dissolving an anionic drug, a cationic compound, an amphiphilic block copolymer and a salt of polylactic acid in a water-miscible organic solvent or a mixed solvent of an aqueous solution and an organic solvent;

(b) removing a layer of organic solvent from the mixture of step (a); and (c) adding an aqueous solution to the mixture from step (b) in which the organic solvent is removed, to form micelles.

Specifically, in step (a), the anionic drug, the cationic compound, the amphiphilic block copolymer and the salt of polylactic acid are mixed within the water-miscible organic solvent or the mixed solvent of an aqueous solution and an organic solvent so as to form a complex. Specifically, the water-miscible organic solvent may be at least one selected from the group consisting of acetone, ethanol, methanol and acetic acid, and the organic solvent in the mixed solvent may be at least one selected from the group consisting of ethyl acetate, acetonitrile, methylene chloride, chloroform and dioxane. The aqueous solution may be distilled water, water for injection or buffer. The mixed ratio of the organic solvent and the aqueous solution in the mixed solvent may not be particularly limited. For example, on the basis of volume, the ratio of the organic solvent and the aqueous solution in the mixed solvent may be 1:0.1 to 50, and more specifically 1:0.5 to 10 (volume of organic solvent:volume of aqueous solution), but it may not be limited thereto.

In step (b), the organic solvent may be removed from the mixture obtained from step (a) by evaporation.

The remaining mixture is dissolved in the aqueous solution in step (c) after the organic solvent is evaporated, whereby the complex of the anionic drug and the cationic compound is entrapped in the micelle structure of the amphiphilic block copolymer and the salt of polylactic acid. The kind and the amount of the aqueous solution are described above.

According to another embodiment, the method may further comprise step (d) for lyophilizing by adding a lyophilization aid, after step (c).

According to another embodiment, the preparing method may further comprise a process for sterilizing the polymer micelle solution from step (c) by using sterile filter, before lyophilizing in step (d).

The lyophilization aid used in an embodiment of the present invention is added to help the lyophilized composition to maintain a form of cake, or to help the composition melt quickly and evenly during the reconstitution process after lyophilization of the amphiphilic block copolymer composition. Specifically, the lyophilization aid may be at least one selected from the group consisting of lactose, mannitol, sorbitol and sucrose. The amount of the lyophilization aid may be 1 to 90 wt %, and more specifically 10 to 60 wt %, based on the total dry weight of the lyophilized composition.

According to the method of an embodiment of the present invention, a composition in which a complex of the anionic drug and the cationic compound is entrapped in the micelle structure of the amphiphilic block copolymer and the salt of polylactic acid is prepared. Specifically, the micelle particle in the prepared composition is stable in blood, and has the particle size of 10 to 200 nm, and specifically 10 to 150 nm.

DETAILED DESCRIPTION TO CARRY OUT THE INVENTION

Hereinafter, the present invention will be explained in detail with reference to the following Examples. However, these Examples are only to illustrate the invention and its scope is not limited thereto in any manner.

[Preparation Example 1] Synthesis of 1,6-Dioleoyl Triethylenetetramide

The title compound was synthesized and identified according to the procedure described in Example 1 of International Publication No. WO 2012-091523.

[Preparation Examples 2 and 3] Polymerization of mPEG-PLA (Monomethoxy Ethylene Glycol-Polylactide) Block Copolymer (A-B)

mPEG-PLA having a number average molecular weight of 5,000-4,000 Dalton was synthesized according to the procedure described in Preparation Example 1 of International Publication No. WO 2012-091523 [Preparation Example 2].

mPEG-PLA block copolymer having a number average molecular weight of 2,000-1,750 Dalton was synthesized according to the same method by using monomethoxy polyethylene glycol (molecular weight of 2,000 Dalton or less, NOF corporation) [Preparation Example 3].

[Preparation Examples 4 and 5] Polymerization of mPEG-PLA-Tocopherol mPEG-PLA-tocopherol (a number average molecular weight of 5,000-4,000-530 Dalton) was obtained according to the procedure described in Preparation Example 2 of International Publication No. WO 2012-091523 [Preparation Example 4].

mPEG-PLA-tocopherol having a number average molecular weight of 2,000-1,750-530 Dalton was obtained according to the same method [Preparation Example 5].

[Preparation Examples 6 and 7] Synthesis of Polylactic Acid (PLA)

PLA (a number average molecular weight of 1,700 Dalton) was obtained according to the procedure described in Preparation Example 8 of Korean Patent No. 1296326, and the yield was 87% [Preparation Example 6].

PLA having a number average molecular weight of 4,000 Dalton was obtained by reacting for 24 hours according to the same method. Purified PLA was confirmed by $^1$H—NMR, and the yield was 85% [Preparation Example 7].

[Preparation Examples 8 and 9] Synthesis of D,L-Polylactic Acid Sodium Salt (PLANa)

150 ml of acetonitrile was added to 100 g of polylactic acid (number average molecular weight of 1,700) obtained from Preparation Example 6 to dissolve the polylactic acid. 150 ml of an aqueous sodium bicarbonate (0.1 g/ml) was slowly added thereto, and the mixture was stirred at 60° C. for 2 hours at 100 rpm. 15 g of sodium chloride was added thereto at room temperature and stirred for melting, and the layer of aqueous solution was removed by using a separatory funnel.

100 ml of distilled water and 10 g of sodium chloride were added to the remaining layer of organic solvent and stirred for melting. The layer of the organic solvent was collected by using a separatory funnel. The organic solvent and distilled water were completely removed by fractional distillation of the obtained layer of organic solvent at 80° C. for 2 hours under vacuum condition.

Thereafter, 150 ml of anhydrous acetone was added thereto to dissolve the polymer, and the undissolved precipitate was removed by filtration separation. Acetone was removed by fractional distillation at 80° C. for 2 hours under vacuum condition. As a result, 69 g of purified polylactic acid sodium salt was obtained. The purified polylactic acid sodium salt was identified by NMR [Preparation Example 8].

Polylactic acid sodium salt was prepared from polylactic acid (number average molecular weight of 4,000) obtained from Preparation Example 7 [Preparation Example 9].

[Comparative Example 1] Preparation of Polymeric Micelle Containing siRNA/1,6-Dioleoyl Triethylenetetramide (dioTETA)/mPEG-PLA-Tocopherol (2 k-1.7 k)

1.89 mg of 1,6-dioTETA (N/P ratio: 18) was dissolved in 94.63 μl of chloroform, and 100 μg of siRNA was dissolved in 80 μl of distilled water. 60 mg of mPEG-PLA-tocopherol (2 k-1.7 k) was dissolved in 200 μl of chloroform. 505.37 μl of chloroform was added until the volume ratio of the organic layer to the aqueous layer reached 10. siRNA was added dropwise to the mixture of solution in which 1,6-dioTETA and mPEG-PLA-tocopherol were dissolved in chloroform, and the mixture was made into emulsion by using a sonicator. The emulsion was added dropwise to 2320 μl of distilled water, and made into a complex emulsion by using a sonicator. The prepared complex emulsion was put into a 1-neck round flask and distilled under reduced pressure in rotary evaporator to selectively remove chloroform so as to prepare polymeric micelles containing siRNA/1,6-dioleoyl triethylenetetramide (dioTETA)/mPEG-PLA-tocopherol (2 k-1.7 k) (see Table 1).

TABLE 1

|  | Composition | Ratio | siRNA | Lipid | Polymer |
|---|---|---|---|---|---|
| Comparative Example 1 | siRNA/dioTETA/mPEG-PLA-tocopherol (2k-1.7k) | 5-18-3 | 100 μg | 1.89 mg | 60 mg |

(The ratio is expressed in the order of the amount of siRNA at μg, N/P ratio and the amount of polymer at mg. The same will be applied to tables hereinafter.)

[Comparative Example 2] Preparation of Polymeric Micelle Containing siRNA/1,6-Dioleoyl Triethylenetetramide (dioTETA)/mPEG-PLA-Tocopherol (2 k-1.7 k)/PLA (1.7 k)

2.52 mg of 1,6-dioTETA (N/P ratio: 16) was dissolved in 126.18 μl of chloroform, and 150 μg of siRNA was dissolved in 120 μl of distilled water. 9 mg of PLA-COOH (1.7 k) was dissolved in 180 μl of chloroform, and 30 mg mPEG-PLA-tocopherol (2 k-1.7 k) was dissolved in 100 μl of chloroform. 813.82 μl of chloroform was added until the volume ratio of the organic layer to the aqueous layer reached 10. 1,564 μl of chloroform was added to 20 μl of the chloroform solution in which 30 mg of mPEG-PLA-tocopherol was dissolved, which corresponded to 6 mg of mPEG-PLA-tocopherol (20 wt %), and the mixture was put into a 1-neck round flask. Thereafter, the solvent was removed by distillation under reduced pressure in a rotary evaporator.

The solution of dioTETA, the solution of PLA and the solution of 24 mg of mPEG-PLA-tocopherol were mixed, and the aqueous solution of siRNA was added dropwise thereto so as to prepare emulsion by using a sonicator. The emulsion was put into a 1-neck round flask coated with 6 mg of mPEG-PLA-tocopherol, and the solvent was removed by distillation under reduced pressure in a rotary evaporator. Polymeric micelle containing siRNA/dioTETA/mPEG-PLA-tocopherol (2 k-1.7 k)/PLA was prepared by adding 3 ml of distilled water to the flask and dissolving by shaking the flask gently (see Table 2).

TABLE 2

|  | Composition | Ratio | siRNA | Lipid | Polymer 1 | Polymer 2 |
|---|---|---|---|---|---|---|
| Comparative Example 2 | siRNA/dioTETA/ mPEG-PLA-tocopherol (2k-1.7k)/PLA (1.7k) | 5-16-1-0.3 | 150 μg | 2.52 mg | 30 mg | 9 mg |

(Polymer 1: mPEG-PLA-tocopherol, Polymer 2: PLA)

[Examples 1 and 2] Preparation of Composition Containing siRNA/1,6-Dioleoyl Triethylenetetramide (dioTETA)/mPEG-PLA-Tocopherol (2 k-1.7 k) /PLANa (1.7 k)

2.52 mg of 1,6-dioTETA was dissolved in 126.18 μl of chloroform, and 150 μg of siRNA was dissolved in 120 μl of distilled water. 9 mg of PLANa (1.7 k) was dissolved in 180 μl of chloroform, and 30 mg mPEG-PLA-tocopherol (2 k-1.7 k) was dissolved in 100 μl of chloroform. 813.82 μl of chloroform was added until the volume ratio of the organic layer to the aqueous layer reached 10. 1,564 μl of chloroform was added to 20 μl of the chloroform solution of 30 mg of mPEG-PLA-tocopherol, which corresponded to 6 mg of mPEG-PLA-tocopherol (20 wt %), and the mixture was put into a 1-neck round flask. Thereafter, the solvent was removed by distillation under reduced pressure in a rotary evaporator.

The solution of dioTETA, the solution of PLANa and the solution of 24 mg of mPEG-PLA-tocopherol were mixed, and the aqueous solution of siRNA was added dropwise thereto so as to prepare emulsion by using a sonicator. The emulsion was put into a 1-neck round flask coated with 6 mg of mPEG-PLA-tocopherol, and the solvent was removed by distillation under reduced pressure in a rotary evaporator.

A composition containing siRNA/dioTETA/mPEG-PLA-tocopherol (2 k-1.7 k)/PLANa was prepared by adding 3 ml of distilled water to the flask and dissolving by shaking the flask gently. Polymeric micelle 2 was prepared in the same manner as above by using different amounts of dioTETA and PLANa.

TABLE 3

|  | Composition | Ratio | siRNA | Lipid | Polymer 1 | Polymer 2 |
|---|---|---|---|---|---|---|
| Example 1 | siRNA/dioTETA/mPEG-PLA-tocopherol (2k-1.7k)/PLANa (1.7k) | 5-16-1-0.3 | 150 μg | 2.52 mg | 30 mg | 9 mg |
| Example 2 | siRNA/dioTETA/mPEG-PLA-tocopherol (2k-1.7k)/PLANa (1.7k) | 5-24-1-0.5 | 150 μg | 3.78 mg | 30 mg | 15 mg |

(Polymer 1: mPEG-PLA-tocopherol, Polymer 2: PLANa)

[Examples 3 to 6] Preparation of Composition Containing siRNA/dioTETA/mPEG-PLA-Tocopherol (2 k-1.7 k)/PLANa (1.7 k)

Compositions 3 to 6 containing siRNA/dioTETA/mPEG-PLA-tocopherol (2 k-1.7 k)/PLANa (1.7 k) were prepared in the same manner as Example 1 by using different amounts of dioTETA or mPEG-PLA-tocopherol (2 k-1.7 k).

The compositions prepared from Examples 3 to 6 are listed in Table 4 below:

TABLE 4

|  | Composition | Ratio | siRNA | Lipid | Polymer 1 | Polymer 2 |
|---|---|---|---|---|---|---|
| Example 3 | siRNA/dioTETA/mPEG-PLA-tocopherol (2k-1.7k)/PLANa (1.7k) | 5-8-1-0.3 | 150 μg | 1.26 mg | 30 mg | 9 mg |
| Example 4 | siRNA/dioTETA/mPEG-PLA-tocopherol (2k-1.7k)/PLANa (1.7k) | 5-24-1-0.3 | 150 μg | 3.79 mg | 30 mg | 9 mg |
| Example 5 | siRNA/dioTETA/mPEG-PLA-tocopherol (2k-1.7k)/PLANa (1.7k) | 5-16-0.5-0.3 | 150 μg | 2.52 mg | 15 mg | 9 mg |
| Example 6 | siRNA/dioTETA/mPEG-PLA-tocopherol (2k-1.7k)/PLANa (1.7k) | 5-16-3-0.3 | 150 μg | 2.52 mg | 90 mg | 9 mg |

(Polymer 1: mPEG-PLA-tocopherol, Polymer 2: PLANa)

[Examples 7 and 8] Preparation of Composition Containing siRNA/dioTETA/mPEG-PLA-Tocopherol (2 k-1.7 k)/PLANa (1.7 k)

Compositions 7 and 8 containing siRNA/dioTETA/mPEG-PLA-tocopherol (2 k-1.7 k)/PLANa (1.7 k) were prepared in the same manner as Example 1 by using different amounts of PLANa (1.7 k) (see Table 5).

TABLE 5

| | Composition | Ratio | siRNA | Lipid | Polymer 1 | Polymer 2 |
|---|---|---|---|---|---|---|
| Example 7 | siRNA/dioTETA/mPEG-PLA-tocopherol (2k-1.7k)/PLANa (1.7k) | 5-16-1-0.1 | 150 μg | 2.52 mg | 30 mg | 3 mg |
| Example 8 | siRNA/dioTETA/mPEG-PLA-tocopherol (2k-1.7k)/PLANa (1.7k) | 5-16-1-0.5 | 150 μg | 2.52 mg | 30 mg | 15 mg |

(Polymer 1: mPEG-PLA-tocopherol, Polymer 2: PLANa)

[Experimental Example 1] Comparison of the Particle Size and the Surface Charge of siRNA/dioTETA/mPEG-PLA-Tocopherol(2 k-1.7 k)/PLANa(1.7 k) Micelle Depending on the Change of the Composition Ratio To confirm the formation of nanoparticles depending on the ratio of siRNA/dioTETA (N/P ratio), the amount of the amphiphilic block copolymer (2 k-1.7 k) and the amount of PLANa (1.7 k), the size and the surface charge of micelles were measured. The particle size was measured by DLS (Dynamic Light Scattering). Specifically, a He-Ne laser was used as a light source, and a Zetasizer Nano ZS90 (MALVERN) was operated according to the manufacturer's instruction.

The size and the surface charge of the micelles of Examples 1 to 4 having different N/P ratios are shown in Table 6 below:

TABLE 6

| | Composition | Ratio | Particle size | Surface charge |
|---|---|---|---|---|
| Example 1 | siRNA/dioTETA/mPEG-PLA-tocopherol (2k-1.7k)/PLANa(1.7k) | 5-16-1-0.3 | 32.67 nm | −5.74 mV |
| Example 2 | siRNA/dioTETA/mPEG-PLA-tocopherol (2k-1.7k)/PLANa(1.7k) | 5-24-1-0.5 | 35.59 nm | −4.31 mV |
| Example 3 | siRNA/dioTETA/mPEG-PLA-tocopherol (2k-1.7k)/PLANa(1.7k) | 5-8-1-0.3 | 22.59 nm | −7.31 mV |
| Example 4 | siRNA/dioTETA/mPEG-PLA-tocopherol (2k-1.7k)/PLANa(1.7k) | 5-24-1-0.3 | 23.79 nm | 3.09 mV |

The size and the surface charge of the micelles of Examples 1, 5 and 6 having different amounts of the amphiphilic block copolymer (2 k-1.7 k) are shown in Table 7 below:

TABLE 7

| Change of the amount of mPEG-PLA-tocopherol (2k-1.7k) | | | | |
|---|---|---|---|---|
| | Composition | Ratio | Particle size | Surface charge |
| Example 1 | siRNA/dioTETA/mPEG-PLA-tocopherol (2k-1.7k)/PLANa(1.7k) | 5-16-1-0.3 | 28.67 nm | −5.74 mV |
| Example 5 | siRNA/dioTETA/mPEG-PLA-tocopherol (2k-1.7k)/PLANa(1.7k) | 5-16-0.5-0.3 | 28.03 nm | −9.16 mV |
| Example 6 | siRNA/dioTETA/mPEG-PLA-tocopherol (2k-1.7k)/PLANa(1.7k) | 5-16-3-0.3 | 23.97 nm | −4.02 mV |

The size and the surface charge of the micelles of Examples 1, 7 and 8 having different amounts of PLANa (1.7 k) are shown in Table 8 below:

TABLE 8

Change of the amount of PLA-COONa (1.7k)

|  | Composition | Ratio | Particle size | Surface charge |
|---|---|---|---|---|
| Example 1 | siRNA/dioTETA/mPEG-PLA-tocopherol (2k-1.7k)/PLANa(1.7k) | 5-16-1-0.3 | 28.67 nm | −5.74 mV |
| Example 7 | siRNA/dioTETA/mPEG-PLA-tocopherol (2k-1.7k)/PLANa(1.7k) | 5-16-1-0.1 | 26.52 nm | 4.2 mV |
| Example 8 | siRNA/dioTETA/mPEG-PLA-tocopherol (2k-1.7k)/PLANa(1.7k) | 5-16-1-0.5 | 24.86 nm | −9.79 mV |

[Examples 9 to 11] Preparation of Composition Containing siRNA/dioTETA/mPEG-PLA-Tocopherol/PLANa Polymeric micelles 9, 10 and 11 were prepared in the same manner as Example 1, except that mPEG-PLA-tocopherol (5 k-4 k) was used instead of mPEG-PLA-tocopherol (2 k-1.7 k), or PLANa (4 k) was used instead of PLANa (1.7 k).

TABLE 9

|  | Composition | Ratio | siRNA | Lipid | Polymer 1 | Polymer 2 |
|---|---|---|---|---|---|---|
| Example 9 | siRNA/dioTETA/mPEG-PLA-tocopherol (5k-4k)/PLANa (1.7k) | 5-16-1-0.3 | 150 μg | 2.52 mg | 30 mg | 9 mg |
| Example 10 | siRNA/dioTETA/mPEG-PLA-tocopherol (2k-1.7k)/PLANa (4k) | 5-16-1-0.3 | 150 μg | 2.52 mg | 30 mg | 9 mg |
| Example 11 | siRNA/dioTETA/mPEG-PLA-tocopherol (5k-4k)/PLANa (4k) | 5-16-1-0.3 | 150 μg | 2.52 mg | 30 mg | 9 mg |

(Polymer 1: mPEG-PLA-tocopherol, Polymer 2: PLANa)

[Experimental Example 2] Comparison of the Particle Size and the Surface Charge of siRNA/dioTETA/mPEG-PLA-Tocopherol/PLANa Micelle According to Change of the Composition and the Composition Ratio The size and the surface charge of the micelles of Examples 1, 9, 10 and 11 were measured in the same manner as Experimental Example 1 to confirm the formation of nanoparticles depending on the molecular weight of the amphiphilic block copolymer and PLA-COONa. The results are shown in Table 10 below:

TABLE 10

|  | Composition | Ratio | Particle size | Surface charge |
|---|---|---|---|---|
| Example 1 | siRNA/dioTETA/mPEG-PLA-tocopherol (2k-1.7k)/PLANa(1.7k) | 5-16-1-0.3 | 28.67 nm | −5.74 mV |
| Example 9 | siRNA/dioTETA/mPEG-PLA-tocopherol (4k-5k)/PLANa(1.7k) | 5-16-1-0.3 | 36.47 nm | −1.54 mV |
| Example 10 | siRNA/dioTETA/mPEG-PLA-tocopherol (2k-1.7k)/PLANa(4k) | 5-16-1-0.3 | 27.49 nm | −0.82 mV |
| Example 11 | siRNA/dioTETA/mPEG-PLA-tocopherol (4k-5k)/PLANa(4k) | 5-16-1-0.3 | 35.4 nm | −0.99 mV |

[Example 12] Preparation of Composition Containing siRNA-Cholesterol/dioTETA/mPEG-PLA-Tocopherol (2 k-1.7 k)/PLANa (1.7 k)

A composition containing siRNA-cholesterol/dioTETA/mPEG-PLA-tocopherol(2 k-1.7 k)/PLANa (1.7 k) was prepared in the same manner as Example 1 by using siRNA-cholesterol. The solvent was removed from the mixture by distillation under reduced pressure in a rotary evaporator. The composition was prepared by adding 3 ml of distilled water to the flask and dissolving by shaking the flask gently.

[Example 13] Preparation of Composition Containing siRNA-PEG/dioTETA/mPEG-PLA-Tocopherol (2 k-1.7 k)/PLANa (1.7 k)

A composition containing siRNA-PEG/dioTETA/mPEG-PLA-tocopherol (2 k-1.7 k)/PLANa (1.7 k) was prepared in the same manner as Example 1 by using siRNA-PEG. The solvent was removed from the mixture by distillation under reduced pressure in a rotary evaporator. The composition was prepared by adding 3 ml of distilled water to the flask and dissolving by shaking the flask gently.

The compositions obtained from Examples 12 and 13 are listed in Table 11 below:

TABLE 11

| | Composition | Ratio | siRNA | Lipid | Polymer 1 | Polymer 2 |
|---|---|---|---|---|---|---|
| Example 12 | siRNA-cholesterol/dioTETA/mPEG-PLA-tocopherol(2k-1.7k)/PLANa (1.7k) | 5-16-1-0.3 | 150 µg | 2.52 mg | 30 mg | 9 mg |
| Example 13 | siRNA-PEG/dioTETA/mPEG-PLA-tocopherol (2k-1.7k)/PLANa (1.7k) | | | | | |

(Polymer 1: mPEG-PLA-tocopherol, Polymer 2: PLANa)

[Example 14] Preparation of Composition Containing siRNA/bPEI/mPEG-PLA-Tocopherol (2 k-1.7 k)/PLANa (1.7 k)

0.3 mg of bPEI was dissolved in 15 µl of distilled water, and 150 µg of siRNA was dissolved in 120 µl of distilled water. The aqueous solution of bPEI and the aqueous solution of siRNA were mixed in 105 µl of HBS aqueous solution (10 mM HEPES, 1 mM NaCl). 9 mg of PLANa (1.7 k) was dissolved in 180 µl of chloroform, and 30 mg mPEG-PLA-tocopherol (2 k-1.7 k) was dissolved in 100 µl of chloroform. 2,140 µl of chloroform was added until the volume ratio of the organic layer to the aqueous layer reached 10. 1,564 µl of chloroform was added to 20 µl of the chloroform solution of 30 mg of mPEG-PLA-tocopherol, which corresponds to 6 mg of mPEG-PLA-tocopherol (20 wt %), and they were put into a 1-neck round flask. Thereafter, the solvent was removed by distillation under reduced pressure in a rotary evaporator.

The solution of PLANa and the solution of 24 mg of mPEG-PLA-tocopherol were mixed, and the HBS aqueous solution containing bPEI and siRNA was added dropwise thereto so as to prepare emulsion by using a sonicator. The emulsion was put into a 1-neck round flask coated with 6 mg of mPEG-PLA-tocopherol, and the solvent was removed by distillation under reduced pressure in a rotary evaporator. A composition containing siRNA/bPEI/mPEG-PLA-tocopherol (2 k-1.7 k)/PLANa (1.7 k) was prepared by adding 6 ml of distilled water to the flask and dissolving by shaking the flask gently (see Table 12).

TABLE 12

| | Composition | Ratio | siRNA | bPEI | Polymer 1 | Polymer 2 |
|---|---|---|---|---|---|---|
| Example 14 | siRNA/bPEI/mPEG-PLA-tocopherol (2k-1.7k)/PLANa (1.7k) | 5-2-1-0.3 | 150 µg | 0.3 mg | 30 mg | 9 mg |

(Polymer 1: mPEG-PLA-tocopherol, Polymer 2: PLANa)

[Examples 15 and 16] Preparation of Composition Containing siRNA/Cationic Lipid/mPEG-PLA-Tocopherol (2 k-1.7 k)/PLANa (1.7 k)

Composition 9 containing siRNA/1,10-dioleoyl pentaethylenehexamide (dioPEHA)/mPEG-PLA-tocopherol (2 k-1.7 k)/PLANa (1.7 k) and composition 10 containing siRNA/1, 8-dilinoleoyl tetraethylenepentamide (dilTEPA)/mPEG-PLA-tocopherol (2 k-1.7 k)/PLANa (1.7 k) were prepared in the same manner as Example 1 by using a different cationic lipid (see Table 13).

TABLE 13

| | Composition | Ratio | siRNA | Lipid | Polymer 1 | Polymer 2 |
|---|---|---|---|---|---|---|
| Example 15 | siRNA/dioPEHA/mPEG-PLA-tocopherol (2k-1.7k)/PLANa (1.7k) | 5-16-1-0.3 | 150 µg | 1.42 mg | 30 mg | 9 mg |
| Example 16 | siRNA/dilTEPA/mPEG-PLA-tocopherol (2k-1.7k)/PLANa (1.7k) | 5-16-1-0.3 | 150 µg | 1.78 mg | 30 mg | 15 mg |

(Polymer 1: mPEG-PLA-tocopherol, Polymer 2: PLANa)

[Examples 17 and 18] Preparation of Composition Containing siRNA-PEG/dioTETA/mPEG-PLA-Tocopherol(2 k-1.7 k)/PLANa (1.7 k)/DOPE(Dioleoylphosphatidylethanolamine)

A composition containing siRNA-PEG/dioTETA/mPEG-PLA-tocopherol (2 k-1.7 k)/PLANa (1.7 k)/DOPE was prepared in the same manner as Example 1 by using siRNA-PEG. DOPE was used in the same amount as, or four times more than, dioTETA. The solvent was removed from the mixture by distillation under reduced pressure in a rotary evaporator. The composition was prepared by adding 3 ml of distilled water to the flask and dissolving by shaking the flask gently (Table 14).

TABLE 14

| | Composition | Ratio | siRNA | Lipid | Polymer 1 | Polymer 2 | DOPE |
|---|---|---|---|---|---|---|---|
| Example 17 | siRNA/dioPEHA/mPEG-PLA-tocopherol (2k-1.7k)/PLANa (1.7k)/DOPE | 5-18-1-0.3-0.1 | 150 µg | 1.42 mg | 30 mg | 9 mg | 1.42 mg |
| Example 18 | siRNA/dilTEPA/mPEG-PLA-tocopherol (2k-1.7k)/PLANa (1.7k)/DOPE | 5-16-1-0.3-0.4 | 150 µg | 1.78 mg | 30 mg | 15 mg | 5.68 mg |

(Polymer 1: mPEG-PLA-tocopherol, Polymer 2: PLANa)

[Experimental Example 3] Comparison of the Size and the Surface Charge of Micelles of siRNA/Cationic Material/Amphiphilic Block Copolymer/PLANa(/DOPE)

The size and the surface charge of the micelles were measured in the same manner as Experimental Example 1 to confirm the formation of nanoparticles depending on the kinds of siRNA and the cationic material, and the presence of PLANa or DOPE. The results are shown in Table 15 below:

TABLE 15

| | Compositions | Ratio | Particle size | Surface charge |
|---|---|---|---|---|
| Comparative Example 1 | siRNA/dioTETA/mPEG-PLA-tocopherol (2k-1.7k) | 5-18-3 | 25.32 nm | 12.37 mV |

TABLE 15-continued

| | Compositions | Ratio | Particle size | Surface charge |
|---|---|---|---|---|
| Comparative Example 2 | siRNA/dioTETA/mPEG-PLA-tocopherol (2k-1.7k)/PLA (1.7k) | 5-16-1-0.3 | 25.71 nm | 5.48 mV |
| Example 1 | siRNA/dioTETA/mPEG-PLA-tocopherol (2k-1.7k)/PLANa (1.7k) | 5-16-1-0.3 | 28.07 nm | −1.29 mV |
| Example 12 | siRNA-cholesterol/dioTETA/mPEG-PLA-tocopherol (2k-1.7k)/PLANa (1.7k) | 5-16-1-0.3 | 27.73 nm | −4.38 mV |
| Example 13 | siRNA-PEG/dioTETA/mPEG-PLA-tocopherol (2k-1.7k)/PLANa (1.7k) | 5-16-1-0.3 | 28.23 nm | −3.09 mV |
| Example 14 | siRNA/bPEI/mPEG-PLA-tocopherol (2k-1.7k)/PLANa (1.7k) | 5-2-1-0.3 | 25.49 nm | −6.46 mV |
| Example 17 | siRNA-PEG/dioTETA/mPEG-PLA-tocopherol (2k-1.7k)/PLANa (1.7k)/DOPE | 5-18-1-0.3-0.1 | 26.21 nm | 1.02 mV |
| Example 18 | siRNA-PEG/dioTETA/mPEG-PLA-tocopherol (2k-1.7k)/PLANa (1.7k)/DOPE | 5-18-1-0.3-0.4 | 25.47 nm | 4.42 mV |

[Experimental Example 4] Analysis of Blood Concentration of Micelles of siRNA/Cationic Material/Amphiphilic Block Copolymer/PLANa The formulation prepared in Experimental Example 1 was administered to animals, and the blood samples were collected 0.5 and 6 hours after administration. The blood concentration of micelles was analyzed by RT (Reverse Transcription) and qRT-PCR (quantitative Reverse Transcription-Polymerase Chain Reaction) as below.

The formulation was intravenously injected into Balb/c mice at 1 mg/kg, and blood was collected after 0.5 and 6 hours, respectively. The blood was centrifuged at 13,000 rpm, 4° C. for 15 minutes, and the supernatant was collected in a new tube. A total of 11 concentrations ranging from 4 μM to 0.00256 μM were prepared in PBS for standard formulations. 1 μl of the diluted standard formulation was added to a 96-well plate for PCR, and 9 μl of Balb/c mouse serum and 90 μl of 0.25% triton X-100 were added thereto. After 90 μl of 0.25% Triton X-100 was added to 10 μl of experimental blood sample, a pretreatment step was carried out to release the delivery system. After the formulation was released, the exposed siRNA was synthesized as cDNA through RT (reverse transcription), and qRT-PCR (Bio-Rad CFX96 Real-Time System) was performed using the synthesized cDNA. Analysis was performed using the Bio-Rad CFX Manager program.

TABLE 16

| | Blood concentration (ng/mL) | |
|---|---|---|
| | 0.5 hours | 6 hours |
| Comparative Example 1 | 1565.6 | 856.82 |
| Comparative Example 2 | 808.43 | 158.75 |
| Example 1 | 7483.83 | 3449.33 |
| Example 2 | 11650.82 | 5362.87 |

As can be seen in Table 16, at 0.5 hours the blood concentration of the formulations prepared in Examples 1 and 2 was 5 to 8 times as high as those of Comparative Examples 1 and 2. Therefore, the stability of the formulation of an embodiment of the present invention in blood was confirmed as being excellent.

[Experimental Example 5] In Vivo Distribution of siRNA/Cationic Material/Amphiphilic Block Copolymer/PLANa Micelle in Tissue The amount of siRNA/dioTETA/mPEG-PLA-tocopherol/PLANa polymeric micelle in liver and cancer tissue in a body was determined.

A2780cis human ovarian cancer cell line was subcutaneously injected into Balb/c nude mice to produce cancer-induced mice. The formulation was intravenously administered at a dose of 1 mg/kg once every two days, four times in total. 24 hours after the last administration, liver and cancer tissue were extracted and weighed 200 mg each, then placed in 1.8 ml of 0.25% Triton X-100 and ground with a tissue grinder. For a standard tissue sample, physiological saline was injected and the tissues were ground in the same manner. A total of 11 concentrations ranging from 4 μM to 0.00256 μM were prepared in PBS for standard formulations. 99 μl of the ground standard tissue and 1 μl of the diluted standard formulation were added to a 96-well plate for PCR. The tissue samples to be analyzed were added in an amount of 100 μl, and a pretreatment step was carried out to release the formulations. The exposed siRNA was synthesized to cDNA through RT (reverse transcription), and qRT-PCR (Bio-Rad CFX96 Real-Time System) was performed using the synthesized cDNA. Analysis was performed using the Bio-Rad CFX Manager program.

The analysis results are shown in Table 17 below.

TABLE 17

| | Tissue concentration (ng/g) | | |
|---|---|---|---|
| | Cancer | Liver | Cancer/Liver ratio |
| Comparative Example 1 | 5.47 | 401.48 | 0.014 |
| Example 2 | 51.04 | 208.45 | 0.245 |

As shown in Table 17, in Example 2 according to an embodiment of the present invention, the distribution of the polymeric micelle was reduced in liver tissue, but increased in cancer tissue as compared with Comparative Example 1. These results suggest that the polymeric micelle containing PLANa of an embodiment of the present invention is able to specifically target cancer tissue.

[Experimental Example 6] In Vivo Activity of siRNA/Cationic Material/Amphiphilic Block Copolymer/PLANa Micelle (Ability for Gene Repression)

In vivo activity of siRNA/dioTETA/mPEG-PLA-tocopherol/PLANa polymeric micelles was determined by measurement of gene repression.

Balb/c nude mice were transplanted with A549 human lung cancer sections to produce cancer-induced mice. The formulations were intravenously administered at a dose of 0.5 mg/kg once every two days, three times in total. Physiological saline was administered to a control. Each formulation was administered to five (5) mice. 24 hours after the last administration, cancer tissues were extracted and initially ground using a mortar bowl in the presence of liquid nitrogen. Thereafter, the tissues were ground again by using QIAGEN homogenizer (TissueLyser). 10 mg of the cancer tissue, which was ground twice, was treated with 600 μl of a prepared working homogenizing solution (Homogenizing solution 600 μl+Proteinase K (23 mg/mL) 6 μl) to expose HPRT mRNA from cells. After preparing the samples as above, they were analyzed by using a bDNA assay kit according to the manufacturer's instruction (analysis method for Panomics bDNA).

GAPDH mRNA, a gene that is not affected by HPRT siRNA, was also analyzed by the same method. The mean values of relative expression of HPRT siRNA in cancer tissues were calculated by correcting the measured amount of HPRT mRNA. The analysis results are shown in Table 18 below.

TABLE 18

|  | Relative expression of HPRT mRNA (%) |
| --- | --- |
| Control | 100 |
| Comparative Example 1 | 98 |
| Example 2 | 46 |

As shown in Table 18, Example 2 according to an embodiment of the present invention inhibited the in vivo expression of mRNA of the target gene HPRT by 54% in cancer.

The invention claimed is:

1. A composition for delivering an anionic drug, comprising:
the anionic drug as an active ingredient;
a cationic compound, which is a cationic lipid represented by Formula 7 as recited below;
an amphiphilic block copolymer; and
at least one salt of a polylactic acid of Formula 1 as below,
wherein the anionic drug forms a complex with the cationic compound by electrostatic interaction,
wherein the complex is entrapped in a micelle structure of the amphiphilic block copolymer and the salt of polylactic acid,
wherein an anion of carboxylic acid in the salt of polylactic acid is bound to the complex in order to reduce the surface charge of the micelle, and
wherein the surface charge of the micelle is from −20 mV to 20 mV:

RO—CHZ—[A]$_n$—[B]$_m$—COOM     [Formula 1]

wherein A is —COO—CHZ—; B is —COO—CHY—; R is a hydrogen atom, or acetyl, benzoyl, decanoyl, 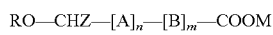 palmitoyl, methyl or ethyl; Z and Y each are methyl; M is Na, K or Li; n is an integer from 1 to 30; and m is an integer from 0 to 20,
wherein the salt of polylactic acid has a number average molecular weight of at least 500 Daltons,

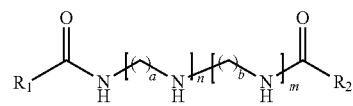
[Formula 7]

wherein n and m each are 0 to 12 with the proviso that 2≤n+m≤12, a and b each are 1 to 6, $R_1$ and $R_2$ each are independently selected from the group consisting of saturated and unsaturated $C_{11-25}$ hydrocarbons.

2. The composition for delivering an anionic drug of claim 1, wherein the anionic drug is a nucleic acid.

3. The composition for delivering an anionic drug of claim 2, wherein the nucleic acid is at least one selected from the group consisting of RNA, DNA, siRNA (short interfering RNA), aptamer, antisense ODN (antisense oligodeoxynucleotide), antisense RNA, ribozyme and DNAzyme.

4. The composition for delivering an anionic drug of claim 1, wherein n and m are independently 1 to 9, with the proviso that 2≤n+m≤10.

5. The composition for delivering an anionic drug of claim 1, wherein a and b are 2 to 4.

6. The composition for delivering an anionic drug of claim 1, wherein $R_1$ and $R_2$ each are independently selected from the group consisting of lauryl, myristyl, palmityl, stearyl, arachidyl, behenyl, lignoceryl, cerotyl, myristoleyl, palmitoleyl, sapienyl, oleyl, linoleyl, arachidonyl, eicosapentaenyl, erucyl, docosahexaenyl and cerotyl.

7. The composition for delivering an anionic drug of claim 1, wherein the ratio of quantities of electric charges of the cationic lipid (N) and the anionic drug (P) (N/P) is 0.1 to 128.

8. The composition for delivering an anionic drug of claim 1, wherein the amphiphilic block copolymer is an A-B type di-block copolymer composed of a hydrophilic A block and a hydrophobic B block, wherein the hydrophilic A block is at least one selected from the group consisting of polyalkyleneglycol, polyvinyl alcohol, polyvinyl pyrrolidone, polyacrylamide and derivatives thereof, and the hydrophobic B block is at least one selected from the group consisting of polyester, polyanhydride, polyamino acid, polyorthoester and polyphosphazine.

9. The composition for delivering an anionic drug of claim 8, wherein a hydroxyl group at the end of the hydrophobic B block is modified by at least one selected from the group consisting of cholesterol, tocopherol and $C_{10-24}$ fatty acid.

10. The composition for delivering an anionic drug of claim 9, wherein the hydrophilic A block has a number average molecular weight of 200 to 50,000 Dalton, and the hydrophobic B block has a number average molecular weight of 50 to 50,000 Dalton.

11. The composition for delivering an anionic drug of claim 1, wherein the ratio of the weight of the complex of the anionic drug and the cationic lipid (a) to the weight of the amphiphilic block copolymer (b)[a/b×100] is 0.001 to 100 wt %.

12. The composition for delivering an anionic drug of claim 1, wherein the salt of polylactic acid has a number average molecular weight of 500 to 50,000 Dalton.

13. The composition for delivering an anionic drug of claim 8, comprising 10 to 1,000 parts by weight of the amphiphilic block copolymer and 5 to 500 parts by weight of the salt of polylactic acid per 1 part by weight of the anionic drug.

14. The composition for delivering an anionic drug of claim 1, further comprising a fusogenic lipid.

15. The composition for delivering an anionic drug of claim 14, wherein the fusogenic lipid is at least one selected from the group consisting of dilauroyl phosphatidylethanolamine, dimyristoyl phosphatidylethanolamine, dipalmitoyl phosphatidylethanolamine, di stearoyl phosphatidylethanolamine, dioleoyl phosphatidylethanolamine, dilinoleoyl phosphatidylethanolamine, 1-palmitoyl-2-oleoyl phosphatidylethanolamine, 1,2-diphytanoyl-3-sn-phosphatidylethanolamine, dilauroyl phosphatidylcholine, dimyristoyl phosphatidylcholine, dipalmitoyl phosphatidylcholine, distearoyl phosphatidylcholine, dioleoyl phosphatidylcholine, dilinoleoyl phosphatidylcholine, 1-palmitoyl-2-oleoyl phosphatidylcholine, 1,2-diphytanoyl-3-sn-phosphatidylcholine, dilauroyl phosphatidic acid, dimyristoyl phosphatidic acid, dipalmitoyl phosphatidic acid, distearoyl phosphatidic acid, dioleoyl phosphatidic acid, dilinoleoyl phosphatidic acid, 1-palmitoyl -2-oleoyl phosphatidic acid, 1,2-diphytanoyl-3-sn-phosphatidic acid, cholesterol and tocopherol.

* * * * *

UNITED STATES PATENT AND TRADEMARK OFFICE
CERTIFICATE OF CORRECTION

| | |
|---|---|
| PATENT NO. | : 11,253,598 B2 |
| APPLICATION NO. | : 15/759943 |
| DATED | : February 22, 2022 |
| INVENTOR(S) | : Hye Yeong Nam et al. |

It is certified that error appears in the above-identified patent and that said Letters Patent is hereby corrected as shown below:

On the Title Page

Please add item (73) after item (72):
-- (73)   Assignee: SAMYANG HOLDINGS CORPORATION, Seoul (KR) --

Signed and Sealed this
Eighteenth Day of October, 2022

Katherine Kelly Vidal
*Director of the United States Patent and Trademark Office*